US00PP28023P2

(12) United States Plant Patent
Koekkoek

(10) Patent No.: US PP28,023 P2
(45) Date of Patent: May 16, 2017

(54) CARNATION PLANT NAMED 'HILBEAKATE'

(50) Latin Name: *Dianthus caryophyllus*
Varietal Denomination: Hilbeakate

(71) Applicant: Arthur N. J. Koekkoek, Alkmaar (NL)

(72) Inventor: Arthur N. J. Koekkoek, Alkmaar (NL)

(73) Assignee: Hilverda Kooij B.V., De Kwakel (NL)

( * ) Notice: Subject to any disclaimer, the term of this patent is extended or adjusted under 35 U.S.C. 154(b) by 41 days.

(21) Appl. No.: 14/545,366

(22) Filed: Apr. 28, 2015

(51) Int. Cl.
*A01H 5/02* (2006.01)

(52) U.S. Cl.
USPC ..... Plt./273

(58) Field of Classification Search
USPC ..... Plt./273
See application file for complete search history.

(56) References Cited

PUBLICATIONS

UPOV hit on *Dianthus* plant named 'Hilbeakate', QZ PBR 20143572, application publication date Feb. 15, 2015.*

* cited by examiner

*Primary Examiner* — Anne Grunberg
(74) *Attorney, Agent, or Firm* — C. A. Whealy

(57) ABSTRACT

A new and distinct cultivar of Carnation plant named 'Hilbeakate', characterized by its compact, uniformly mounding and upright to broadly spreading plant habit; relatively small leaves; freely flowering habit; flat red purple-colored flowers with a single whorl of petals; and good container performance.

1 Drawing Sheet

Botanical designation: *Dianthus caryophyllus.*
Cultivar denomination: 'HILBEAKATE'.

CROSS-REFERENCED TO CLOSELY-RELATED APPLICATIONS

Title: Carnation Plant Named 'Hilbeanaom'
Applicant: Arthur N. J. Koekkoek
Filed: Apr. 28, 2015
U.S. Plant patent application Ser. No.: 14/545,367

BACKGROUND OF THE INVENTION

The present invention relates to a new and distinct cultivar of Carnation plant, botanically known as *Dianthus caryophyllus*, grown commercially as a container plant and hereinafter referred to by the name 'Hilbeakate'.

The new Carnation plant is a product of a planned breeding program conducted by the Inventor in De Kwakel, The Netherlands. The objective of the breeding program is to create new container Carnation plants with numerous flat flowers with a single whorl of petals.

The new Carnation plant originated from a cross-pollination made by the Inventor in De Kwakel, The Netherlands in June, 2010 of *Dianthus caryophyllus* 'Kahori', not patented, as the female, or seed, parent with a proprietary selection of *Dianthus caryophyllus* identified as code number A66180-03, not patented, as the male, or pollen, parent. The new Carnation plant was discovered and selected by the Inventor as a single flowering plant from within the progeny of the stated cross-pollination in a controlled greenhouse environment in De Kwakel, The Netherlands in September, 2011.

Asexual reproduction of the new Carnation plant by terminal cuttings propagated in a controlled greenhouse environment in De Kwakel, The Netherlands since October, 2011 has shown that the unique features of this new Carnation plant are stable and reproduced true to type in successive generations of asexual reproduction.

SUMMARY OF THE INVENTION

Plants of the new Carnation have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilbeakate'. These characteristics in combination distinguish 'Hilbeakate' as a new and distinct Carnation plant:

1. Compact, uniformly mounding and upright to broadly spreading plant habit.
2. Relatively small leaves.
3. Freely flowering habit.
4. Flat red purple-colored flowers with a single whorl of petals.
5. Good container performance.

Plants of the new Carnation differ from plants of the female parent, 'Kahori' , in the following characteristics:

1. Plants of the new Carnation have larger flowers than plants of 'Kahori'.
2. Plants of the new Carnation have longer peduncles than plants of 'Kahori'.
3. Flower petals of plants of the new Carnation are red purple in color whereas flower petals of plants of 'Kahori' are dark pink purple in color.

Plants of the new Carnation differ from plants of the male parent selection in the following characteristics:

1. Plants of the new Carnation have single-type flowers whereas plants of the male parent selection have semi-double flowers.
2. Flower petals of plants of the new Carnation are red purple in color whereas flower petals of plants of the male parent selection are darker red purple in color.

Plants of the new Carnation can be compared to plants of *Dianthus caryophyllus* 'Hilbeanaom', disclosed in U.S. Plant patent application Ser. No. 14/545,367. Plants of the new Carnation differ primarily from plants of 'Hilbeanaom' in flower color as plants of the new Carnation have darker red purple-colored flowers than plants of 'Hilbeanaom'.

Plants of the new Carnation can also be compared to plants of *Dianthus caryophyllus* 'Twinkle', not patented. In side-by-side comparisons, plants of the new Carnation differed primarily from plants of 'Twinkle' in the following characteristics:

1. Plants of the new Carnation had larger flowers than plants of 'Twinkle'.
2. Flower petals of plants of the new Carnation were red purple in color whereas flower petals of plants of 'Twinkle' were red in color.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant.

The photograph comprises a side perspective view of a typical flowering plant of 'Hilbeakate' grown in a container.

DETAILED BOTANICAL DESCRIPTION

Plants used in the aforementioned photograph and following observations and measurements were grown during the winter in 10.5-cm containers in a glass-covered greenhouse in De Kwakel, The Netherlands and under cultural practices typical of commercial container Carnation production. During the production of the plants, day temperatures ranged from 12° C. to 15° C., night temperatures averaged 12° C. and light levels averaged 7,000 lux. Plants were pinched one time five weeks after planting. Plants used for the photograph and description were 20 weeks old. In the following description, color references are made to The Royal Horticultural Society Colour Chart, 2007 Edition, except where general terms of ordinary dictionary significance are used.

Botanical classification: *Dianthus caryophyllus* 'Hilbeakate'.

Parentage:

*Female, or seed, parent.*—*Dianthus caryophyllus* 'Kahori', not patented.

*Male, or pollen, parent.*—Proprietary selection of *Dianthus caryophyllus* identified as code number A66180-03, not patented.

Propagation:

*Type.*—By terminal cuttings.

*Time to initiate roots, summer.*—About six days at temperatures ranging from 20° C. to 25° C.

*Time to initiate roots, winter.*—About eight days at temperatures about 18° C.

*Time to produce a rooted young plant, summer.*—About three weeks at temperatures ranging from 20° C. to 25° C.

*Time to produce a rooted young plant, winter.*—About five weeks at temperatures about 18° C.

*Root description.*—Medium in thickness, fibrous; whitish in color.

*Rooting habit.*—Moderate branching; medium density.

Plant description:

*Plant and growth habit.*—Herbaceous perennial, typically grown as a container plant; compact, uniformly mounding, upright to broadly spreading plant habit; low vigor.

*Plant height, soil level to top of foliar plane.*—About 6 cm.

*Plant height, soil level to top of floral plane.*—About 10.3 cm.

*Plant diameter or spread.*—About 19.6 cm.

*Lateral branches.*—Branching habit: Freely branching habit with about six main (basal) stems; each main stem with about eight lateral branches. Length, main stems: About 3 cm. Length, lateral branches: About 6.5 cm. Diameter, main stems and lateral branches: About 1.5 mm. Internode length: About 4 cm. Number of internodes per stem: About three. Strength: Strong. Aspect: Main stems, mostly upright; lateral branches, about 35° from the main stem. Cross-section: Circular; solid. Texture: Smooth, glabrous. Luster: Slightly glossy. Color: Close to 145B; older stems, close to 199A and 199B.

Leaf description:

*Arrangement.*—Opposite, simple; sessile.

*Length.*—About 3.3 cm.

*Width.*—About 4 mm.

*Shape.*—Narrowly oblanceolate to lanceolate.

*Apex.*—Acute.

*Base.*—Attenuate; decurrent.

*Margin.*—Entire.

*Texture, upper and lower surfaces.*—Smooth, glabrous.

*Luster, upper and lower surfaces.*—Matte.

*Venation pattern.*—Parallel.

*Color.*—Developing leaves, upper surface: Close to 137B; towards the base, close to 143C. Developing leaves, lower surface: Close to 137C; towards the base, close to 143C. Fully expanded leaves, upper surface: Close to between N137C and 147A; venation, same as lamina, close to between N137C and 147A. Fully expanded leaves, lower surface: Close to N137B; venation, close to 143A.

Flower description:

*Flower form and flowering habit.*—Terminal single-type flat flowers arranged singly, in pairs or in panicles with three to four flowers each; freely flowering habit with numerous flowers developing during the flowering season; flowers face mostly upright to outwardly.

*Natural flowering season.*—Flowering is continuous from the summer to late summer in The Netherlands; plants begin flowering about twelve weeks after planting.

*Postproduction longevity.*—Flowers last about ten days on the plant; flowers not persistent.

*Fragrance.*—Faintly fragrant; clove-like, sweet.

*Flower buds*.—Length: About 1.5 cm. Diameter: About 4.5 mm. Shape: Oblong; styles extruded. Color: Close to 177A; apex, close to 147A.

*Inflorescence height*.—About 7.8 cm.

*Inflorescence diameter*.—About 3.3 cm.

*Flower diameter*.—About 3.5 cm.

*Flower depth*.—About 2.7 cm.

*Petals*.—Quantity and arrangement: About five petals arranged in a single whorl. Length: About 3.5 cm. Width: About 2.1 cm. Shape: Spatulate. Apex: Praemorse, slightly crinkled. Base: Acute. Margin: Entire. Texture, upper and lower surfaces: Smooth, glabrous; velvety. Luster, upper and lower surfaces: Matte. Color: When opening, upper surface: Close to N74B; towards the base, close to 157B. When opening, lower surface: Close to N74C to N74D; towards the base, close to 157B. Fully opened, upper surface: Close to between 72B and N74B; towards the base, close to 157C; color does not fade with development. Fully opened, lower surface: Close to between 72C and N74C; towards the base, close to 157C; color does not fade with development.

*Sepals*.—Quantity and arrangement: About five in a single whorl; proximal 66% portion of the sepals are fused into a campanulate-shaped calyx; epicalyx, adpressed to the calyx; outer lobes are roughly deltoid in shape with long acute apices and inner lobes are roughly deltoid in shape with medium to long acute apices. Length: About 1.8 cm. Width, at base of "free" portion: About 3 mm. Shape: Oblong. Apex: Broadly acute. Margin: Entire. Texture, upper and lower surfaces: Smooth, glabrous. Luster, upper and lower surfaces: Matte. Color: When opening, upper surface: Close to between 146D and 147D. When opening, lower surface: Close to 177A; towards the apex, close to 147A. Fully opened, upper surface: Close to between 146D and 147D. Fully opened, lower surface: Close to 147A; towards the base and apex, close to 177A.

*Peduncles*.—Length: About 4.1 cm. Diameter: About 2 mm. Strength: Strong. Aspect: Erect to about 25° from vertical. Texture: Smooth, glabrous. Color: Close to between 137A and N137D.

*Pedicels*.—Length: About 1.2 cm. Diameter: About 1.5 mm. Strength: Strong. Aspect: Erect to about 30° from the peduncle axis. Texture: Smooth, glabrous. Color: Close to 147A.

*Reproductive organs*.—Stamens: Quantity: About ten per flower. Filament length: About 5 mm. Filament color: Close to 157D. Anther length: About 1 mm. Anther shape: Narrowly oblong. Anther color: Close to 155A. Pollen: None produced. Pistils: Quantity: About two per flower. Pistil length: About 2.5 cm. Stigma shape: Pointed, curved. Stigma color: Close to N155D. Style length: About 2.3 cm. Style color: Close to NN155D. Ovary shape: Obovoid. Ovary texture: Smooth to slightly ribbed. Ovary color: Close to 144B. Fruits and seeds: Fruit and seed development have not been observed on plants of the new Carnation.

Disease & pest resistance: Plants of the new Carnation have not been observed to be resistant to pathogens and pests common to Carnation plants.

Temperature tolerance: Plants of the new Carnation have been observed to tolerate high temperatures about 35° C. and to be hardy to USDA Hardiness Zone 9.

It is claimed:

1. A new and distinct Carnation plant named 'Hilbeakate' as illustrated and described.

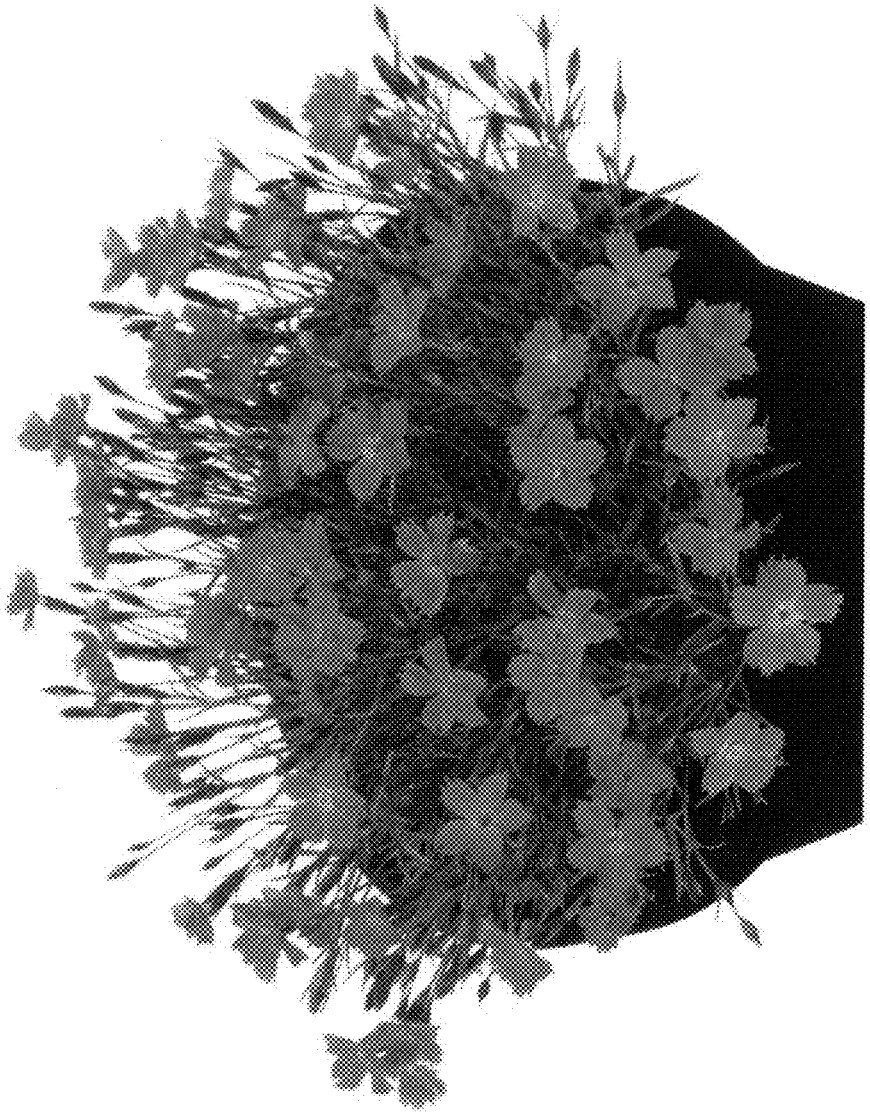

* * * * *